US009962220B2

(12) United States Patent
Domankevitz

(10) Patent No.: US 9,962,220 B2
(45) Date of Patent: May 8, 2018

(54) MODULAR AESTHETIC TREATMENT HANDPIECE

(71) Applicant: LUMENIS LTD., Yokneam Ilit (IL)

(72) Inventor: Yacov Domankevitz, Zichron Yaacov (IL)

(73) Assignee: LUMENIS LTD., Yokneam (IL)

( * ) Notice: Subject to any disclaimer, the term of this patent is extended or adjusted under 35 U.S.C. 154(b) by 92 days.

(21) Appl. No.: 14/696,507

(22) Filed: Apr. 27, 2015

(65) Prior Publication Data

US 2015/0306419 A1    Oct. 29, 2015

Related U.S. Application Data

(60) Provisional application No. 61/984,792, filed on Apr. 27, 2014.

(51) Int. Cl.
| | |
|---|---|
| *A61H 1/00* | (2006.01) |
| *A61B 18/14* | (2006.01) |
| *A61B 18/12* | (2006.01) |
| *A61N 7/00* | (2006.01) |
| *A61B 18/00* | (2006.01) |
| *A61B 18/20* | (2006.01) |
| *A61B 17/00* | (2006.01) |
| *A61B 18/22* | (2006.01) |

(52) U.S. Cl.
CPC .......... *A61B 18/1402* (2013.01); *A61B 18/12* (2013.01); *A61B 18/203* (2013.01); *A61B 18/20* (2013.01); *A61B 2017/00761* (2013.01); *A61B 2018/0016* (2013.01); *A61B 2018/0047* (2013.01); *A61B 2018/00172* (2013.01); *A61B 2018/00178* (2013.01); *A61B 2018/00291* (2013.01); *A61B 2018/00452* (2013.01); *A61B 2018/1467* (2013.01); *A61B 2018/225* (2013.01); *A61N 7/00* (2013.01)

(58) Field of Classification Search
CPC .............................. A61N 7/00; A61H 23/0245
See application file for complete search history.

(56) References Cited

U.S. PATENT DOCUMENTS

| | | | | |
|---|---|---|---|---|
| 7,113,821 | B1 * | 9/2006 | Sun | A61B 5/14514 424/489 |
| 2004/0010268 | A1 * | 1/2004 | Gabehart | A61B 17/54 606/131 |
| 2004/0220622 | A1 * | 11/2004 | Bernabei | A61H 7/008 607/3 |
| 2007/0203447 | A1 * | 8/2007 | Jun | A61B 18/203 604/20 |

(Continued)

*Primary Examiner* — Hien Nguyen
(74) *Attorney, Agent, or Firm* — ISUS Intellectual Property PLL; A. Jason Mirabito

(57) ABSTRACT

A modular energy application device for skin tissue treatment includes a first module, the first module including one or more skin treatment electrodes oriented on a surface to contact the skin tissue; a device to connect the first module to a source of electrical power and control; at least a second module, the second module including one or more treatment electrodes oriented on a surface to contact the skin tissue; a connection device to couple the first and the second modules; an electrical connection device to electrically couple the first and second electrodes; electrical power applied to the electrodes of the first module also applies electrical power to the electrodes of the second module.

3 Claims, 9 Drawing Sheets

(56) References Cited

U.S. PATENT DOCUMENTS

| | | | | |
|---|---|---|---|---|
| 2010/0049177 A1* | 2/2010 | Boone, III | ........... | A61H 9/0057 |
| | | | | 606/9 |
| 2013/0041408 A1* | 2/2013 | Dinville | ............. | A61B 17/7065 |
| | | | | 606/249 |
| 2014/0343574 A1* | 11/2014 | Ignon | ................... | A61B 17/545 |
| | | | | 606/131 |
| 2015/0303619 A1* | 10/2015 | Kockx | ................... | A61N 1/048 |
| | | | | 607/149 |

* cited by examiner

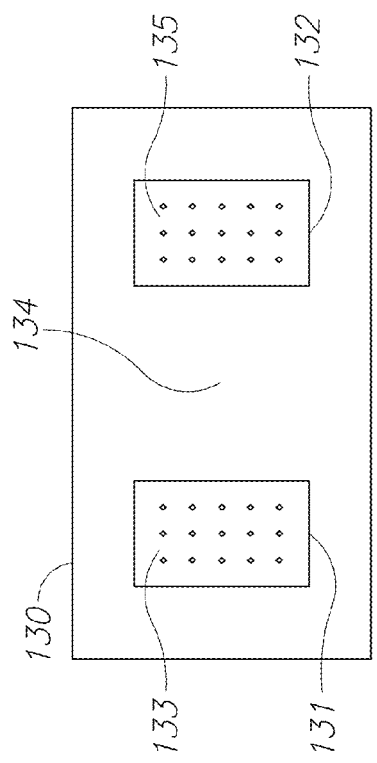
FIG.6
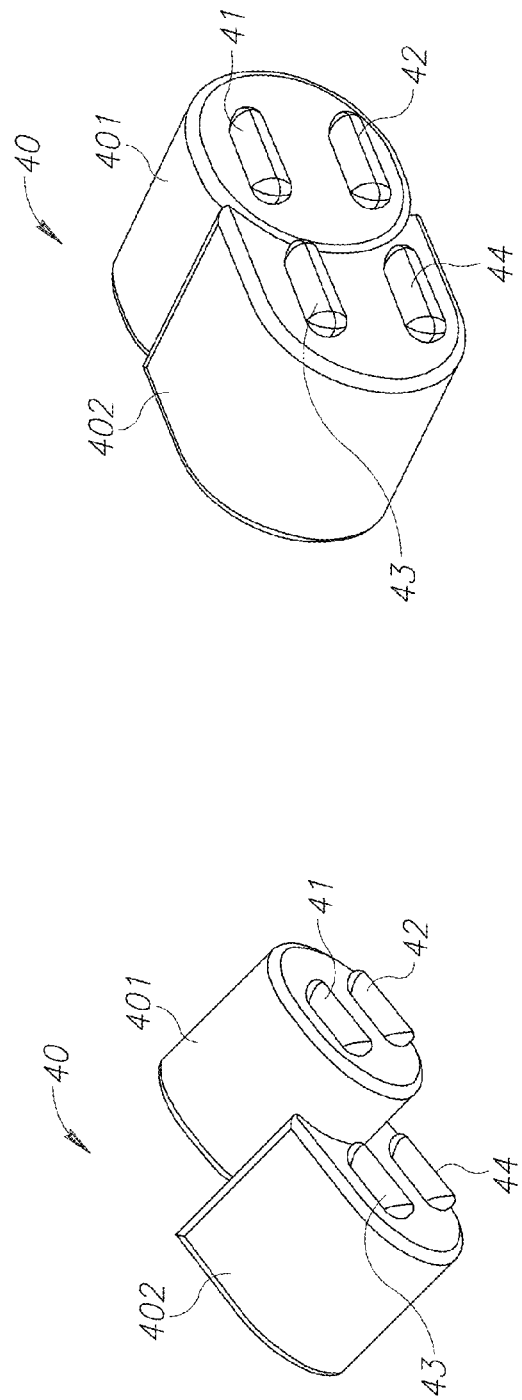
FIG.7B
FIG.7A

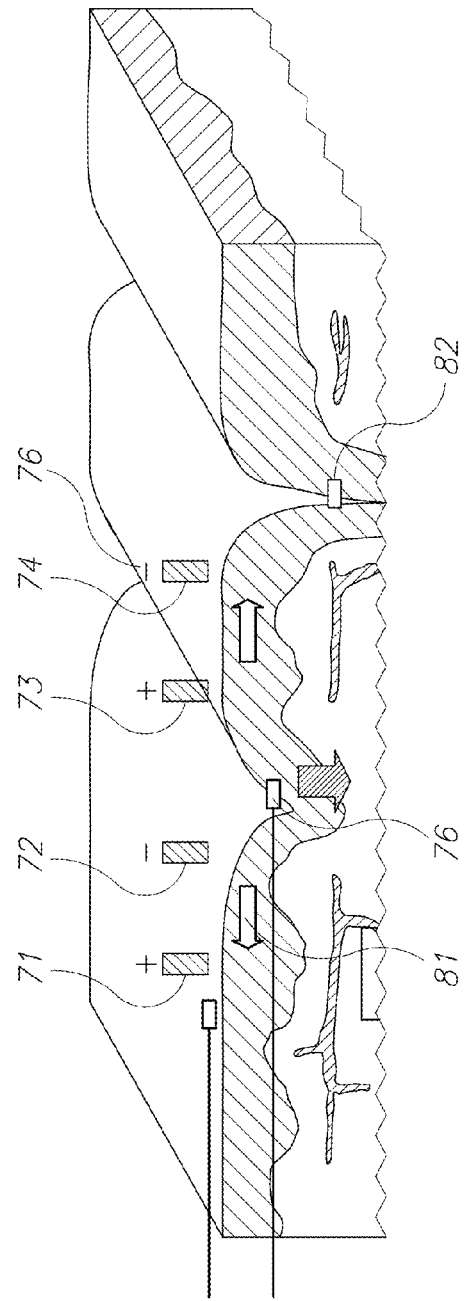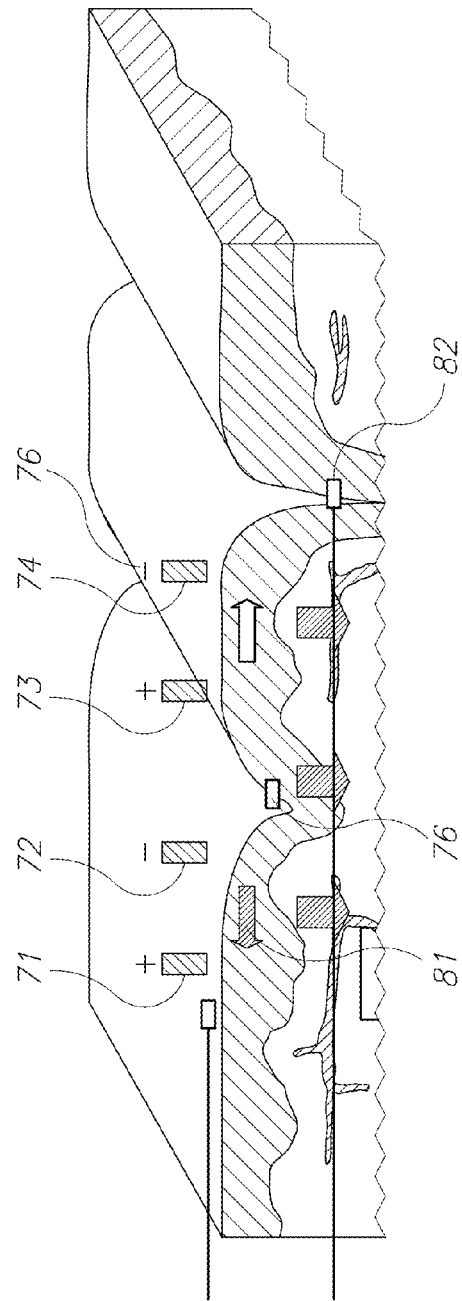

MODULAR AESTHETIC TREATMENT HANDPIECE

RELATED APPLICATIONS

This application claims priority to U.S. provisional application No. 61/984,792, filed Apr. 27, 2014, the entire disclosure of which is incorporated by reference.

FIELD OF THE INVENTION

This invention relates to aesthetic devices and in particular to aesthetic devices employing radio frequency (RF) energy as well as other electromagnetic waves for the purpose of treatment of human skin surfaces to remove or at least decrease wrinkles, lines and folds.

BACKGROUND OF THE INVENTION

A wide variety of aesthetic treatment handpieces has been disclosed in the prior art. Electromagnetic waves such as light, radio frequency (RF) and microwaves are known energy sources in the prior art for treating human skin. Non-electromagnetic energy sources such as ultrasound, shockwaves and cryogenic sources are also common in the aesthetic industry in general and more particularly in the treatment of skin. Whatever the technology utilized, most of these systems have in common some sort of applicator device which applies the particular technology to the human skin.

In fact, combinations of multiple energy sources are known and incorporated into in a single handpiece, and may comprise the same type of energy or a combination of different energy types. These combinations may include a plurality of small energy sources configured to deliver a patterned fractional treatment effect or may be a smaller number of larger energy sources configured to deliver either a more focused and/or bulk treatment of large skin surfaces. Energy may be delivered or applied to different skin organs invasively or non-invasively. In some cases, the handpiece may itself incorporate the mechanism to generate the applied energy while in other cases the handpiece may only deliver and couple energy from a source which is external to the handpiece.

Aesthetic and skin treatments are applied to different body areas. Some body areas are large, uniform, relatively flat and easy to access, like the abdominal area or the calf, while others are not. Small treatment areas like the face may pose a challenge due to the basic size and geometry of the treatment handpiece. Challenges of accessibility to the skin surface may result in less than desired treatment efficiency. Serving the need to treat different types of body areas has been often met in currently available devices in the industry by providing a single main unit to which multiple and different handpieces may be connected. This appears to be a major element in some companies' business model which force their customers to acquire multiple handpieces to accomplish multiple tasks. Alternatively, some companies provide handpieces that have a fixed structure of energy sources and geometry while having a modular energy coupling element which may better access problematic areas. Since treatment efficiency is highly dependent on the energy distribution within the skin and on the energy interaction with different skin organs, treatment handpieces are optimized for their intended uses and, as such, have very limited flexibility or modularity.

Thus, what is needed in the industry are handpiece structures which obviate most if not all of the shortcomings of the presently available devices. It is the subject of the present invention to teach an alternative approaches and treatment handpiece structures.

SUMMARY OF THE PRESENT INVENTION

In a first aspect, a modular energy application device for skin tissue treatment includes a first module, the first module including one or more skin treatment electrodes oriented on a surface to contact the skin tissue; a device to connect the first module to a source of electrical power and control; at least a second module, the second module including one or more treatment electrodes oriented on a surface to contact the skin tissue; a connection device to couple the first and the second modules; an electrical connection device to electrically couple the first and second electrodes; electrical power applied to the electrodes of the first module also applies electrical power to the electrodes of the second module. The number of modules may be greater than two.

In another aspect, a controller connects to the source of electrical power and control to control the application of electrical power to the first and at least the second modules; the first module is mechanically connected to the at least second module; the mechanical connection is one of a slide on or a snap on connection; the first module may be magnetically connected to the at least second module; the slide on connection may include a groove on one of the modules and a slide on the other of the modules.

In a further aspect, the controller detects the presence of the at least second module and is configured to supply electrical power to the at least second module one of equal or non-equal to the electrical power supplied to the first module.

In yet another aspect, the one or more skin treatment electrodes of the first module and the at least second modules are RF electrodes. Each of the electrodes of the first and the at least second module may be elongated with a longitudinal axis and wherein the longitudinal axes of the electrodes of the first and at least second module are arranged parallel to each other.

In another aspect, one or more openings in at least the first module on the surface which contacts the skin tissue, the one or more openings being connectable to a source of vacuum to draw the electrodes to the skin tissue. A second energy source may be included which is not RF. The second energy source may be selected from one or more of a light source or an ultrasound source. The light source may be selected from one or more of a: laser, LED and a flashlamp.

In yet a further aspect, the device may include one or more skin manipulating devices to stretch the skin tissue. Further, the one or more electrodes of the first module may be RF electrodes and the one or more electrodes of the second module are one or more fractional electrodes. The fractional electrodes may be fractional rollers.

In a further aspect, a method of applying an energy application device for skin tissue treatment includes: providing an elongated module, the elongated module including one or more skin treatment electrodes oriented on a surface to contact the skin tissue; and wherein the one or more skin treatment electrodes are elongated and oriented on the surface with their elongated axes in tandem; the one or more skin treatment electrodes being operatively connected to a controller and a source of power; wherein the elongated module is oriented on the skin tissue such that the longitudinal axis of the elongated module is approximately perpendicular to the tissue fold or wrinkle; further comprising applying electrical power to the one or more skin treatment electrodes in contact with the skin tissue for one or more of skin tightening or collagen remodeling treatments.

In yet another aspect, a modular energy application device for skin tissue treatment includes: a first module, the first module including one or more skin treatment electrodes oriented on a surface to contact the skin tissue; a device to connect the first module to a source of electrical power and control; at least a second module, the second module including one or more treatment devices oriented on a surface to contact the skin tissue; a connection device to couple the first and the second modules; an electrical connection device to electrically couple the one or more skin treatment electrodes and the one or more treatment devices; electrical power applied to the electrodes of the first module also applies electrical power to the one or more treatment devices of the second module.

In a further aspect, the one or more skin treatment electrodes may include one or more RF electrodes and the one or more treatment devices may include one or more dermabrasion devices configured to remove or thin the stratum corneum.

In yet another aspect, a method of applying an energy application device for skin tissue treatment includes: providing a treatment module, the module including one or more skin treatment electrodes oriented on a surface to contact the skin tissue and one or more skin dermabrasion devices; the one or more skin treatment electrodes and the one or more dermabrasion devices being operatively connected to a controller and a source of power; further comprising applying electrical power to the one or more dermabrasion devices to one of remove or thin the stratum corneum of the skin tissue; further comprising applying electrical power to the one or more treatment electrodes after the step of applying electrical power to the one or more dermabrasion devices for one or more of skin tightening or collagen remodeling treatments. The one or more skin treatment electrodes may comprise RF electrodes.

BRIEF DESCRIPTION OF THE DRAWINGS

FIG. 6 illustrates an applicator incorporating a fractional energy source.

FIGS. 7a, 7b, 8a and 8b illustrate modular energy source applicators.

FIGS. 11 and 12 illustrate the operation of the energy sources of FIGS. 10a and 10b on skin tissue.

DETAILED DESCRIPTION OF THE PRESENT INVENTION

Figure 1:
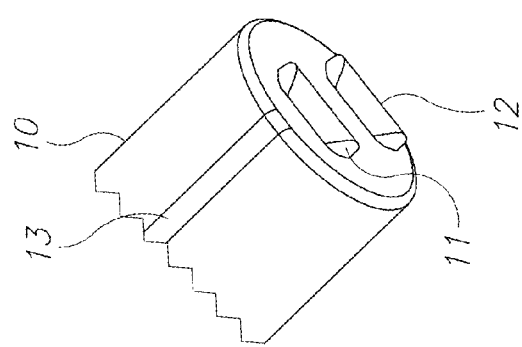
FIG. 1 illustrates skin treatment unit.

According to one aspect of the present invention, a unit treatment cell is disclosed. The unit treatment cell may be designed to apply and distribute energy into the target skin area in a uniform manner as far as such is as possible. Turning now to FIG. 1, that figure illustrates a circular-shaped unit treatment cell 10 having two energy sources 11 and 12. These energy sources may be of any type but for the sake of discussion they may be considered to be RF sources.

Figure 2A:
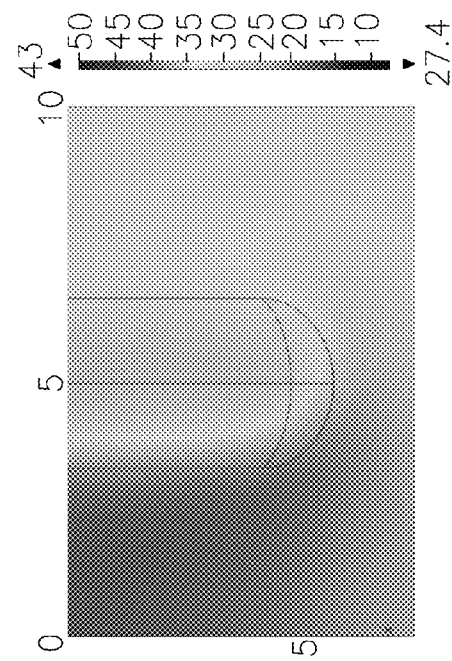
FIGS. 2a, 2b, 3a and 3b illustrate energy distributions using the device of FIG. 1.
Figure 2B:
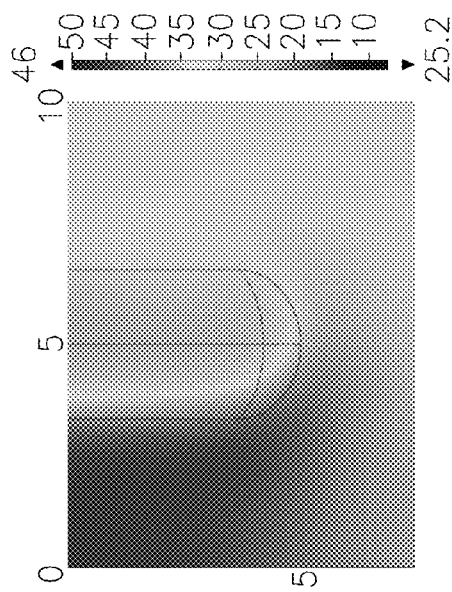
Figure 3A:
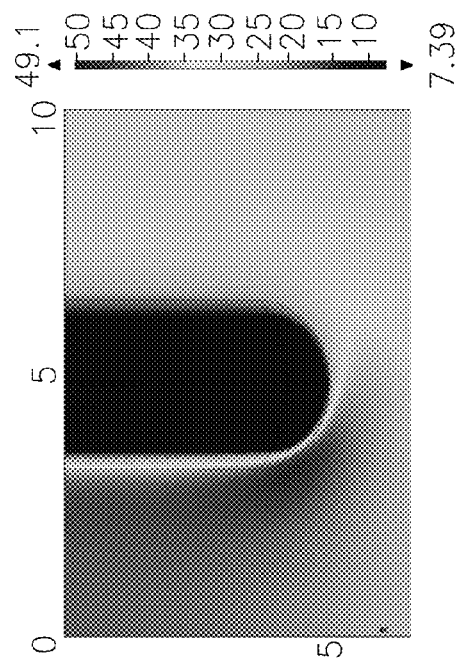
Figure 3B:
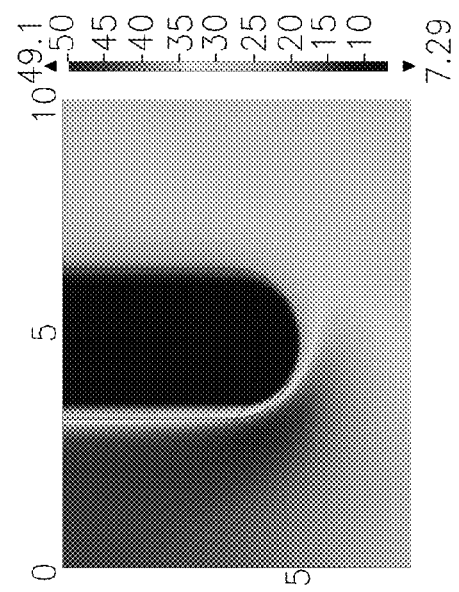

FIGS. 2a, 2b, 3a and 3b illustrate the relatively uniform energy distribution produced by the device of FIG. 1. FIGS. 2a and 3a correspond to first energy source 11 in FIG. 1 and FIGS. 2b and 3b correspond to second energy source 12 of FIG. 1. FIGS. 2a and 2b illustrate energy distribution within the skin from energy sources 11 and 12 at a depth of 1.5 mm. FIGS. 3a and 3b illustrate the energy distribution within the skin from energy sources 11 and 12 at a depth of about 0.5 mm into the skin tissue. Energy sources 11 and 12 are cooled to an about 5 degree centigrade. Energy sources are designed with round curves to avoid sharp edges or points which may cause hot spots in the tissue due to high electrical field concentration. The electrodes according to this aspect of the invention create relatively homogenous RF field in the tissue avoiding hot spots. The cooled electrodes establishes the lowest temperature experienced by the tissue adjacent the electrodes. Heat is accumulated and built by the RF field generated by a unit cell electrodes in the tissue volume between the electrodes. Homogenous temperature distribution allows homogenous tissue effect and a uniform treatment.

Figure 4B:
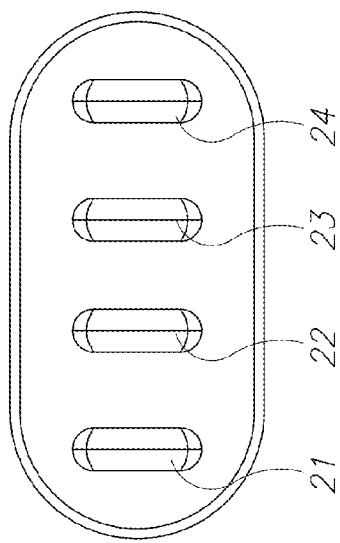
FIGS. 4a and 4b illustrate an applicator using four energy sources.
Figure 5B:
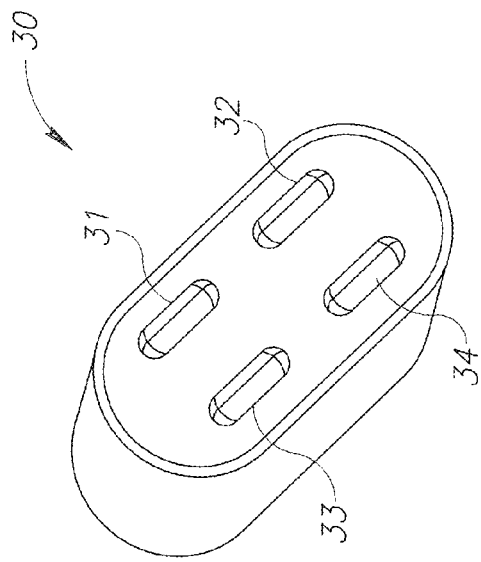
FIGS. 5a and 5b illustrate an alternative arrangement of four energy sources.
Figure 4A:
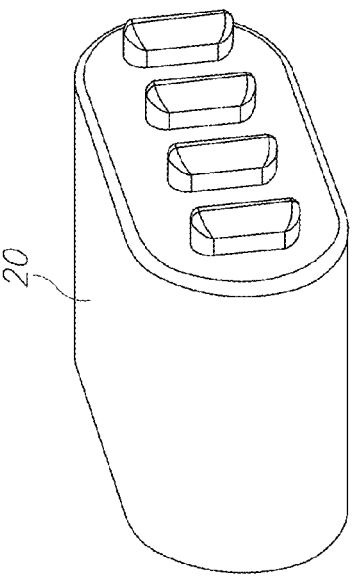
Figure 5A:
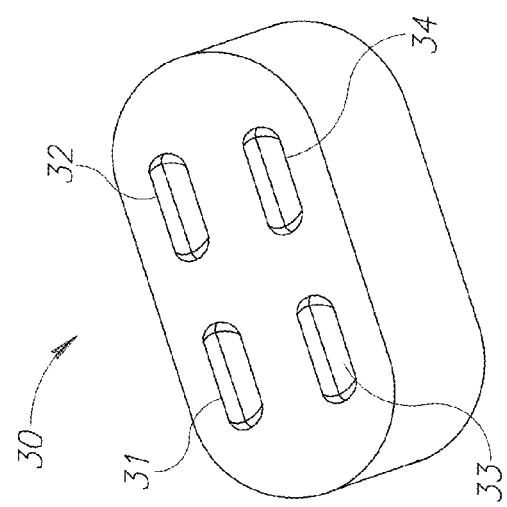

According to another embodiment of the present invention, FIGS. 4a and 4b illustrate in a perspective and bottom view an example of an oval-shaped unit treatment applicator 20 having four energy sources 21, 22, 23, and 24. Any other geometries or number of energy sources may alternatively be provided. In yet another embodiment, FIGS. 5a and 5b illustrate another oval-shaped treatment applicator 30 which includes electrodes 31, 32, 33 and 34 which are arranged in an orientation rotated about ninety degrees from the electrodes as illustrated in FIGS. 4a and 4b. These alternative arrangements of electrodes may be made to accommodate different portions of the human body skin surface to which treatment is to be applied.

Alternatively, a treatment cell unit 130, as shown in FIG. 6, may include at least one fractional RF energy electrode unit 131 and/or 132, with each unit having at least one fractional energy source 133/135. A fractional treatment cell unit is configured to leave a gap 134 of untreated tissue.

According to another aspect of the present invention, multiple treatment application units may be connected in a modular form to produce different sizes and shapes of treatment handpieces. By combining multiple treatment cell units the user may add or reduce the number of energy sources in a handpiece. Such a modular and configurable handpiece may allow, among other things, the applicator operator to better adjust and optimize the handpiece geometry and treatment to the targeted skin area.

Turning now to FIGS. 7a and 7b, these figures illustrate an exemplary configuration of one form of modular treatment applicator. A treatment applicator 40 includes a secondary treatment cell unit 402 in operable connection with a main treatment applicator 401. Electrodes 43 and 44 are positioned in secondary applicator module 402 and electrodes 41 and 42 in main applicator module 401. The electrodes in modules 40 and 402 are elongated and have a longitudinal axis along their elongation. As shown in FIG. 7a, the electrodes 41, 42, 43 and 44 are arranged in a parallel orientation on their longitudinal axes. The two modules may be connected mechanically in a slide and groove arrangement so that the secondary module 402 may be slid from the position in FIG. 7a to the position in 7b, effectively doubling the area of treatment and the number of electrodes. According to another embodiment, the two modules may be connected by a magnetic connector. Such a magnetic connector may couple the two modules mechanically and/or electronically. It is to be understood that more than one secondary treatment applicator module may be connected in a similar fashion either directly to main treatment applicator or indirectly (serially) a third treatment module may be connected to the main treatment module through one of the secondary treatment modules. The main treatment cell unit 401 includes a connector (not shown) that provides connection, which may be an electrical cord, to a source of electrical power and a main control system or controller (also not shown). The secondary treatment applicator 402 and the main treatment cell unit may be provided with electrical connections when they are, for example, in the position shown in FIG. 7b. Once the secondary treatment cell unit is attached to the main treatment cell unit per FIG. 7a, the main control system may be arranged to detect the presence of the secondary treatment cell unit and allow the physician, through the operating system and user interface, to control and adjust treatment parameters to such a secondary treatment cell unit as well as the main treatment cell unit.

In operation of the embodiment of FIGS. 7a and 7b, moving the secondary treatment applicator unit 402 up and down, that is, from the position of FIG. 7a to that of position FIG. 7b may change its operational state from active to inactive. A slidable secondary treatment cell unit provides another degree of flexibility to the user to better adjust the handpiece configuration to the target tissue even after the attachment of such a secondary unit. FIG. 7a shows the secondary treatment applicator 402 in an up position. In this position, the secondary treatment applicator is in an inactive mode and is not configured to deliver energy to the tissue. By sliding down the secondary treatment applicator 402, as shown in FIG. 7b, the operating mode is switched to active and the combined applicators are configured to deliver treatment to the target tissue.

Figure 8B:
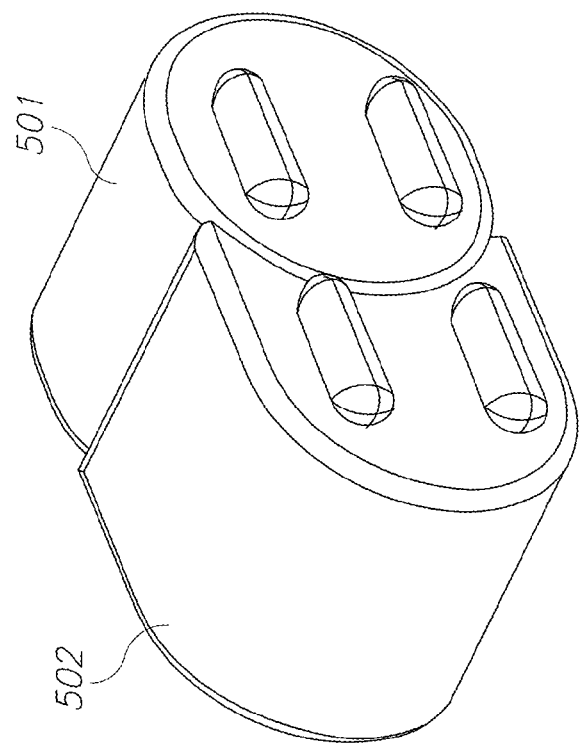
Figure 8A:
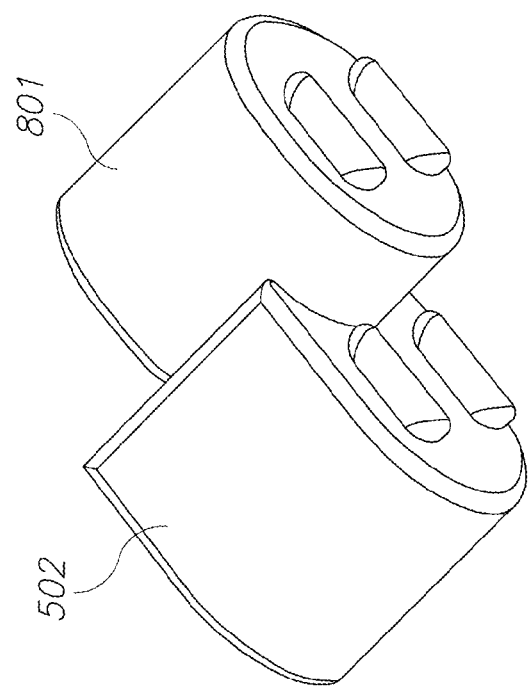

FIGS. 8a and 8b illustrate alternative embodiments of the devices of FIGS. 7a and 7b. In FIGS. 8a and 8b, the secondary applicator 502 may be arranged to "snap" into and onto main applicator 502 using known mechanical elements. Again, additional secondary applicators may be "ganged" to a desired number of applicators according to the design of the operator and the configuration of the body surface to be treated.

Figure 9A:
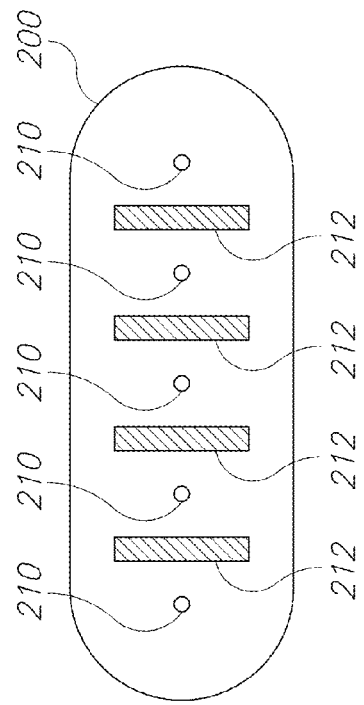
FIGS. 9a, 9b, 9c and 9d illustrate alternative energy applicators.

According to yet another embodiment of the present invention illustrated in FIGS. 9a-9d, a treatment applicator may include one or more energy sources such as light, RF electrodes or ultrasound transducers in a single applicator. The applicator may include any combination thereof. As shown in FIG. 9a, treatment applicator 110 may include a first type of energy source 111 and 112 such as RF or Ultrasound and a second type of energy source 113 such as a laser diode, LED or a wave guide coupled to a flashlamp and configured to deliver light energy to the target tissue.

Figure 9B:
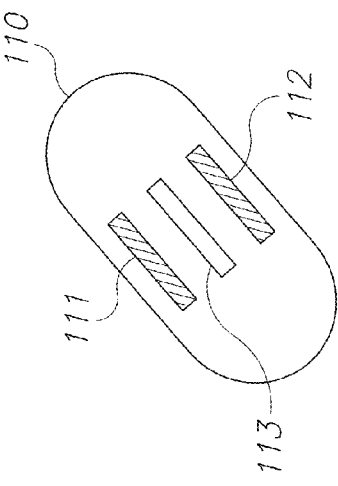
Figure 9C:
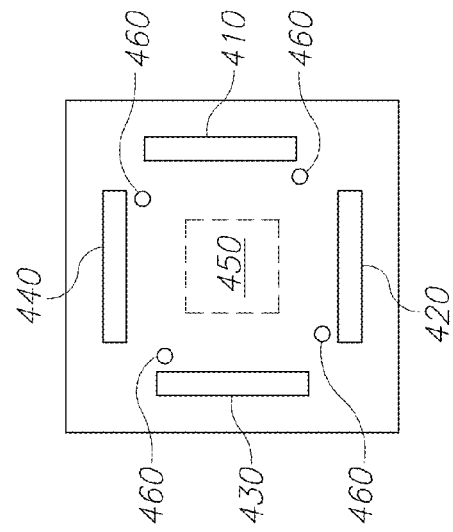
Figure 9D:
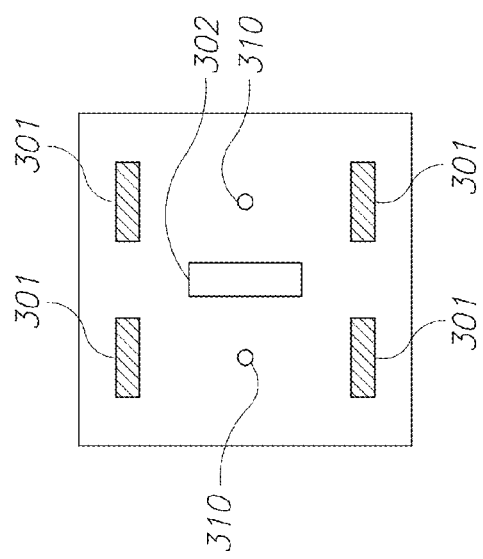

According to another aspect of the present invention illustrated in FIGS. 9b and 9c, skin manipulating elements such as 210 and 310 shown in treatment cell units 200 and 300 respectively may be incorporated in order to protrude or stretch the skin. Such skin manipulating elements may be for example vacuum channels which are in fluid communication with a vacuum pump or mechanical tweezers or pinchers (not shown). Treatment applicator 200 illustrates a first set of energy sources 212 configured to deliver at least one type of energy to the target tissue interdisposed with skin manipulating elements 210. Treatment applicator 300 illustrates a first set of energy sources 301 configured to deliver a first type of energy to the target tissue such as RF and/or ultrasound and a second type energy source 302 configured to deliver a second type of energy to the target tissue such as a light energy Element 400 of FIG. 9d illustrates another non-limiting example of a treatment applicator having a first set of energy sources 410, 420, 430 and 440 configured to deliver a first energy type to the target tissue and at least one second type of energy source 450 configured to deliver a second type of energy to the target tissue. Elements 460 are optionally skin manipulating elements which may improve skin coupling to energy sources or alternatively may mechanically manipulate the target tissue e.g., by stretching or protruding so that the target tissue, while treated by the energy sources, will be at a different mechanical state than its natural mechanical state.

Figure 10A:
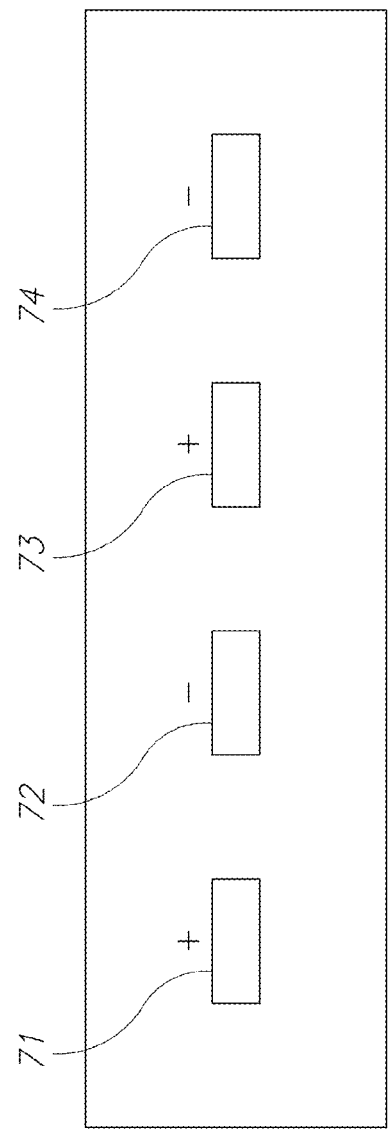
FIGS. 10a and 10b illustrate serial/tandem arrangement of energy sources.
Figure 10B:
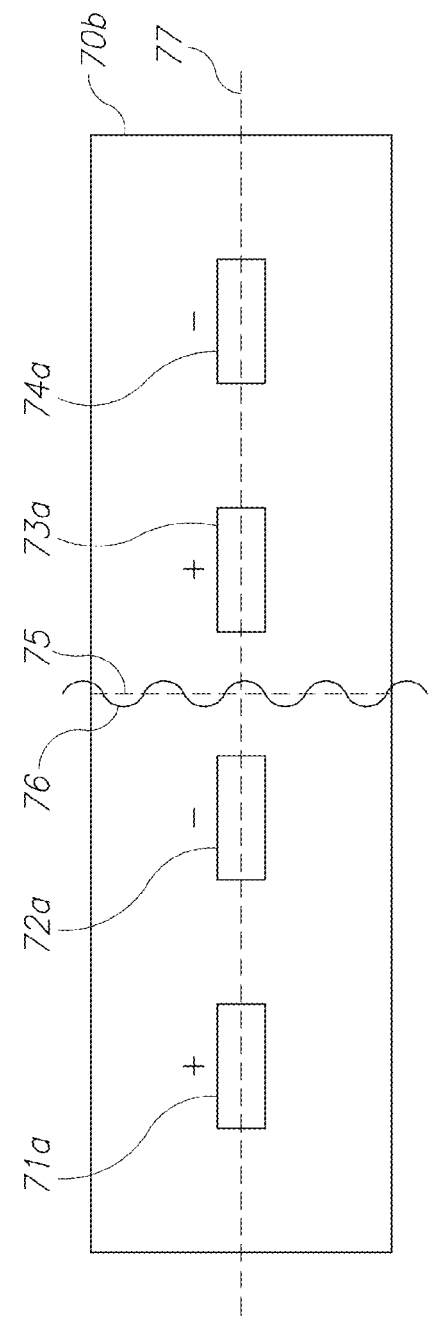

Referring now to FIGS. 10a and 10b, a serial/tandem embodiment of RF electrodes is disclosed in accordance with another aspect of the present invention. RF electrodes 71, 72, 73 and 74 are configured treat a target area in the skin such as for example a line, a wrinkle or a fold. An energy generation system and a controller in the console (not shown) is configured to drive electrodes 71, 72, 73 and 74 in order to deliver RF energy into the target tissue once the handpiece is placed in contact with the skin. Energy sources in a treatment applicator or in a combined treatment applicator may be paired during operation to deliver the required tissue effect. For example, FIG. 10a illustrates pairing electrodes 71 and 72, 72 and 73 and 73 and 74 in order to deliver treatment parameters to achieve a skin rejuvenation effect. FIG. 10b illustrates the same two electrodes 71a and 72a which are paired together with different treatment parameters to achieve a skin tightening effect. A combination treatment of skin tightening effect and a skin rejuvenation effect is also shown in FIG. 10b.

Figure 13:
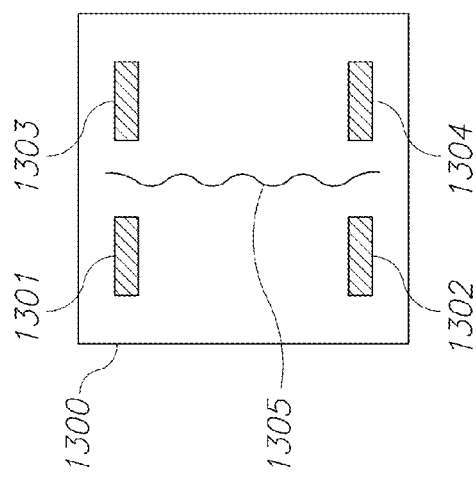
FIG. 13 illustrates an alternative arrangement of electrodes in a skin treatment applicator.

FIG. 11 shows the clinical rationale behind the treatment scheme shown in FIG. 10b. According to this aspect of the invention, at least one serial four electrode treatment applicator like that shown in FIG. 10b is applied on skin deformation 75 characterized along a longitudinal axis 76, both of which are illustrated in FIG. 10b. The four electrodes treatment applicator 70b of FIG. 10b is characterized as having a longitudinal axis 77 (FIG. 10b). The treatment applicator is applied to the skin deformation area so that its axis 77 is approximately perpendicularly to the longitudinal axis 76 of such a skin deformation while the main longitudinal axis 76 of the skin deformation is located somewhere between electrodes 72 and 73. Pairing electrodes 71 and 72 and electrodes 73 and 74 and driving them to provide a skin tightening effect may stretch the tissue as shown by the opposing white arrows 81 and 82 in FIG. 11. Pairing electrodes 72 and 73 and driving them to deliver a skin rejuvenation tissue effect may cause a collagen remodeling effect below the skin deformation zone. As is known, skin tightening effects may be achieved using a higher treatment energy than the energy for collagen remodeling. FIG. 12 illustrates the treatment scheme represented in FIG. 10a in which all electrodes are paired and driven to provide a skin rejuvenation effect only. FIG. 13 illustrates yet another configuration of a treatment apparatus 1300 having four energy sources 1301, 1302, 1303 and 1304 applied to skin deformation 1305.

Different operation regimes may result in different clinical effects. An RF electrode, according to one embodiment of the present invention, may be in the size of an about 1-5 mm in width and 5-15 in length. Distance between electrodes may be in the range of 3-10 mm. According to one embodiment of the present invention the electrode's width may be approximately 3 mm and electrode's length may be approximately 10 mm and the distance between two adjacent electrodes may be about 6 mm. Energy penetration depth into the tissue typically may be approximately ½ the distance between electrodes. A 6 mm distance provides a penetration depth of an about 3 mm. According to one aspect of the present invention, the target area in the skin may be the collagen-rich dermis layer which extends for a depth of up to an about 2-3 mm.

Working parameters for a single treatment applicator according to one aspect of the present invention may be 0.5 sec-10 sec in pulse duration and 10 W-100 W in power. Treatment applicators contained in a handpiece may be driven serially or in parallel. According to another aspect of the present invention, the electrodes may be cooled before, during or after the energy is delivered into the tissue. The handpiece may also incorporate other cooling elements in addition to or instead of the cooled electrodes. In some cases, the continuation or even the overlap between treatment zones in the skin are important to the overall clinical effect. Since the footprint of the handpiece is bigger than the effective treatment area—the area of skin existing between energy sources and that is exposed to the treatment energy—it may be useful to mark the effective treatment area in order to know where to position the handpiece next. A solid pinching or protruding element on the handpiece may be configured to leave a mark on the skin for that purpose.

Figure 14B:
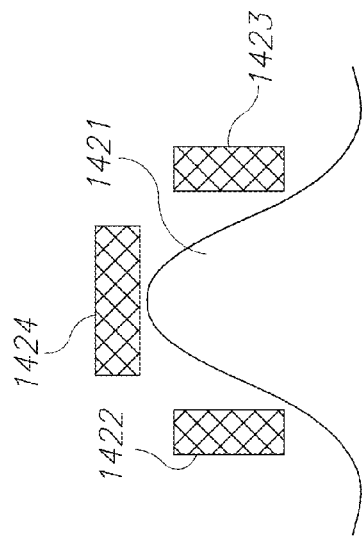
FIGS. 14a and 14b illustrate arrangements of energy source applicators as applied to a 3D volume of skin tissue.
Figure 14A:
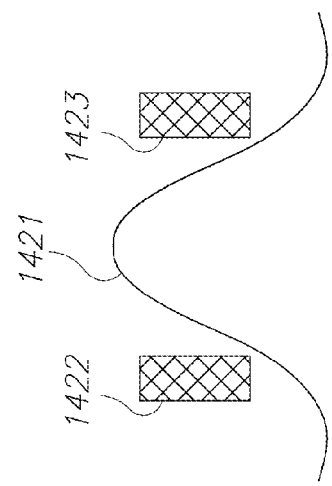

According to yet another aspect of the present invention, treatment applicators may be combined to provide a combined 2D treatment area or alternatively to provide a combined 3D treatment cavity which are configured to fold or capture a fold of the target tissue. FIG. 14a illustrates a 3D treatment area 1421 treated by a 3D handpiece configuration having two treatment applicators 1422 and 1423. FIG. 14b illustrates the same 3D treatment area 1421 treated by a 3D handpiece configuration having three treatment applicators 1422, 1423 and 1424. Electrodes in opposing treatment applicators, such as 1422 and 1423 in FIG. 14a or 1422 and 1423 in FIG. 14b may pair adjacent electrodes in the same applicator or alternatively may pair opposing electrodes from opposed cell units. Big treatment area such as the abdomen may be covered by a single handpiece incorporating 10-20 treatment applicators. Different applications may dictate different sizes of applicators. For example, for skin tightening effects, 10 mm electrodes may be required with a distance of 6 mm between paired electrodes while for body contouring 10 mm electrodes may be required to be a distance of 10 mm between paired electrodes. A 10 mm distance may yield about 5 mm energy penetration depth which may be useful and effective in targeting fat tissue.

Figure 15:
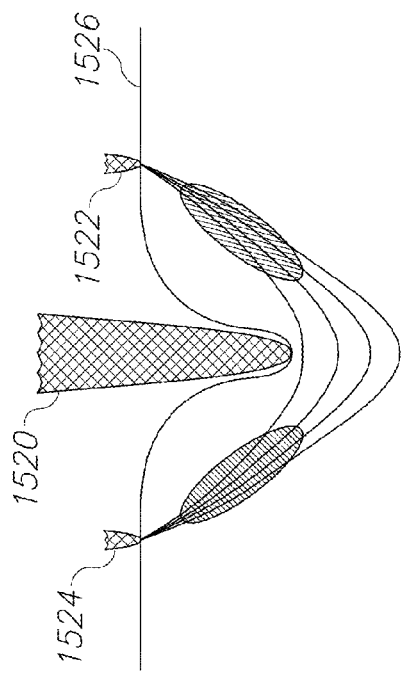
FIG. 15 illustrates an embodiment including a pin to achieve deeper penetration of energy from an energy applicator.

In yet another embodiment illustrated in FIG. 15, a deeper penetration of skin surface may be achieved by placing a pin or other object 1520 between electrodes 1522 and 1524 and pressing down on the pin or other object to lower the skin treatment surface below that of top surface 1526. Since RF energy from electrodes 1524 to 1526 passes under the skin surface, the positioning of the pin or other object will cause deeper penetration below the top surface 1526 of the skin.

According to another aspect of the present invention, an RF treatment according to any of the embodiments mentioned above is delivered to the tissue following a skin pre-treatment. Such a skin pre-treatment may be for example a microdermabrasion treatment which aims to remove the stratum corneum layer of the skin. The stratum corneum thickness of a human body, in most areas, is about 10-20 microns. The impedance of the startum corneum, relative to other skin layers, is higher. This high impedance dictates high voltage RF regime for an effective treatment which targets layers of the skin below the stratum corneum. Some prior art non-invasive RF devices ablate at least a portion of the stratum corneum in order to deliver enough energy into the epidermis. According to this aspect of the invention, a pre-treatment removes the stratum corneum of the skin in order to reduce the electrical impedance of the treated skin area. Such a dermabrasion pre-treatment can be delivered by any common dermabrasion method known to those skilled in the art such as, but not limited to, mechanical, chemical or optical methods. According to another aspect of the present invention, the modular treatment applicator may include a dermabrasion module in conjunction to an RF module so that prior to the placement and activation of the RF module, the dermabrasion module will remove the startum corneum layer of the skin in the target skin area to be treated. The RF module can then treat the skin with lower energies with or without any ablation to the skin areas which are in contact with the electrodes.

Figure 16B:
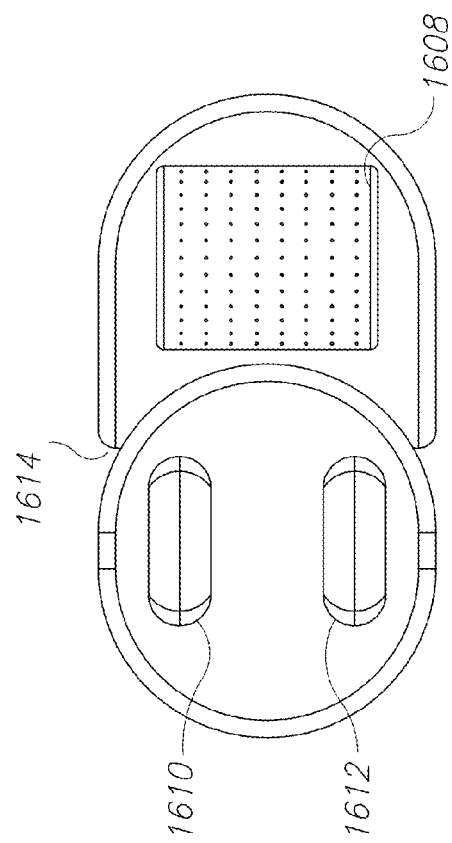
FIGS. 16a and 16b illustrate an applicator combining energy sources with a dermabrasion unit to remove the stratum corneum.
Figure 16A:
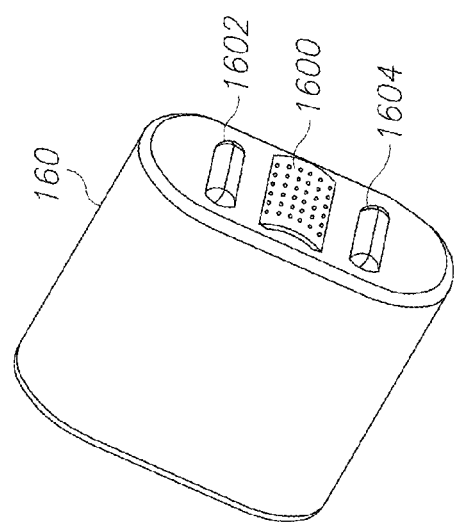

Embodiments in FIGS. 16a and 16b illustrate combinations of application electrodes with a dermabrasion units. In FIG. 16a, a dermabrasion unit 1600 of a known type is shown positioned between two application electrodes 1602 and 1604 in handpiece 1606. The electrodes 1602 and 1604 may be any of the electrodes described in the present application. In operation of the device of FIG. 16a, the dermabrasion unit 1600 may be energized to, among other things, remove the stratum corneum prior to energizing the electrodes 1602 and 1604. These electrodes may be RF electrodes such that once the stratum cornea is removed or thinned out, the RF electrodes may be activated. In the device of FIG. 16b, since the dermabrasion unit 1608 and the application electrodes 1610 and 1612 are arranged in tandem fashion in handpiece 1614, depending on the direction 1616 of movement of the handpiece, the dermabrasion unit may be employed to remove or thin the stratum corneum before treatment by electrodes 1610 and 1612 (which may be RF electrodes) to achieve the results and treatment parameters desired by the operator.

What we claim is:

1. A modular energy application device for skin tissue treatment comprising:
   a first module, the first module including one or more dermabrasion devices configured to remove or thin a stratum corneum portion of the skin tissue, the one or more dermabrasion devices being oriented on a surface to contact the stratum corneum portion of the skin tissue;
   a second module, the second module including a plurality of RF skin treatment electrodes oriented on a surface to contact the skin tissue and provide one or more of skin tightening or collagen remodeling;
   an arrangement to mechanically couple the first and the second modules together to form a single unit through a slide on arrangement wherein the slide on arrangement includes a groove on one of the modules and a slide on the other of the modules;
an electrical connection device to electrically couple the plurality of RF skin treatment electrodes and the one or more dermabrasion devices;
the plurality of RF skin treatment electrodes and the one or more dermabrasion devices being operatively connected to a controller and a source of electrical power;
wherein the plurality of RF skin treatment electrodes of the second module are elongated and wherein the electrodes of the second module are arranged parallel to each other;
wherein the second module containing the plurality of RF skin treatment electrodes is positioned in tandem with the first module;
wherein the parallel axes of the plurality of RF skin treatment electrodes in the second module are in line with the one or more dermabrasion devices in the first module; and
wherein the controller first causes application of the source of electrical power to the one or more dermabrasion devices to remove or thin the stratum corneum and second causes the application of the source of electrical power to the plurality of RF skin treatment electrodes to cause skin tightening or collagen remodeling.

2. The device of claim 1 wherein the controller is configured to supply electrical power to the at least second module one of equal or non-equal to the electrical power supplied to the first module.

3. A method of applying a modular energy application device for skin tissue treatment, the method comprising:
providing a first module, the first module including one or more dermabrasion devices configured to remove or thin a stratum corneum portion of the skin tissue, the one or more dermabrasion devices being oriented on a surface to contact the skin tissue;
providing a second module, the second module including a plurality of RF skin treatment electrodes oriented on a surface to contact the skin tissue and provide one or more of skin tightening or collagen remodeling;
wherein an arrangement to mechanically couples the first and the second modules together to form a single unit through a slide on arrangement wherein the slide on arrangement includes a groove on one of the modules and a slide on the other of the modules;
wherein an electrical connection device to electrically couples the plurality of RF skin treatment electrodes and the one or more dermabrasion devices;
wherein the plurality of RF skin treatment electrodes and the one or more dermabrasion devices are operatively connected to a controller and a source of electrical power;
wherein the plurality of RF skin treatment electrodes of the second module are elongated and wherein the electrodes of the second module are arranged parallel to each other;
wherein the second module containing the plurality of RF skin treatment electrodes is positioned in tandem with the first module;
wherein the parallel axes of the plurality of RF skin treatment electrodes in the second module are in line with the one or more dermabrasion devices in the first module; and
wherein the method further comprises the controller first causing application of the source of electrical power to the one or more dermabrasion devices to remove or thin the stratum corneum and second causing the application of the source of electrical power to the plurality of RF skin treatment electrodes to cause skin tightening or collagen remodeling.

* * * * *